(12) United States Patent
Yabuhara et al.

(10) Patent No.: US 11,209,197 B2
(45) Date of Patent: Dec. 28, 2021

(54) REFRIGERATING/HEATING DEVICE, AND ANALYSIS DEVICE

(71) Applicant: Hitachi High-Technologies Corporation, Tokyo (JP)

(72) Inventors: Tadao Yabuhara, Tokyo (JP); Terumi Tamura, Tokyo (JP); Hiroshi Watanabe, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 313 days.

(21) Appl. No.: 16/313,521

(22) PCT Filed: Jun. 28, 2016

(86) PCT No.: PCT/JP2016/069116
§ 371 (c)(1),
(2) Date: Dec. 27, 2018

(87) PCT Pub. No.: WO2018/003009
PCT Pub. Date: Jan. 4, 2018

(65) Prior Publication Data
US 2020/0182518 A1    Jun. 11, 2020

(51) Int. Cl.
*F25B 21/02*    (2006.01)
*F25D 11/02*    (2006.01)
*F25D 23/12*    (2006.01)

(52) U.S. Cl.
CPC .............. *F25B 21/02* (2013.01); *F25D 11/02* (2013.01); *F25D 23/12* (2013.01)

(58) Field of Classification Search
CPC .................................. F25B 21/02; F25B 21/04
See application file for complete search history.

(56) References Cited

U.S. PATENT DOCUMENTS 3,216,204 A * 11/1965 Milligan ................. F25B 21/02
62/3.2
5,027,145 A *  6/1991 Samuels ................. F25B 21/02
396/573
(Continued)

FOREIGN PATENT DOCUMENTS

JP         36-19944 B1     10/1961
JP         62-73079 A       4/1987
(Continued)

OTHER PUBLICATIONS

International Search Report (PCT/ISA/210) issued in PCT Application No. PCT/JP2016/069116 dated Sep. 13, 2016 with English translation (four (4) pages).
(Continued)

*Primary Examiner* — Filip Zec
(74) *Attorney, Agent, or Firm* — Crowell & Moring LLP

(57) ABSTRACT

The present invention provides a refrigerating/heating device that efficiently refrigerates and heats while suppressing device costs. This refrigerating/heating device for efficiently heating and refrigerating is provided with: a refrigeration chamber; a Peltier-type cooler for supplying cold air to inside the refrigeration chamber; a heat radiation member for radiating Peltier heat; fans for air-cooling the heat radiation member; an exhaust duct through which waste heat from the fans and the heat radiation member passes; and an installation part to which a subject to be heated can be installed. The subject to be heated is installed in the waste heat flow path of the exhaust duct and heated.

8 Claims, 5 Drawing Sheets

(56) References Cited

U.S. PATENT DOCUMENTS

| | | | | |
|---|---|---|---|---|
| 5,588,300 | A * | 12/1996 | Larsson | F25B 21/02 165/185 |
| 5,970,719 | A * | 10/1999 | Merritt | A47J 36/2433 62/3.2 |
| 6,038,865 | A * | 3/2000 | Watanabe | A23L 3/36 62/258 |
| 9,513,037 | B2 * | 12/2016 | Barot | B62J 33/00 |
| 9,786,395 | B2 * | 10/2017 | Singh | G21D 3/04 |
| 9,797,628 | B2 * | 10/2017 | Adler | F25B 3/00 |
| 10,717,344 | B2 * | 7/2020 | Strashny | F25B 27/02 |
| 2003/0029173 | A1 * | 2/2003 | Bell | F24F 5/0042 62/3.3 |
| 2006/0059933 | A1 * | 3/2006 | Axakov | B60H 1/32011 62/244 |
| 2006/0218937 | A1 | 10/2006 | Park | |
| 2006/0288709 | A1 * | 12/2006 | Reidy | F25B 21/02 62/3.4 |
| 2007/0234742 | A1 * | 10/2007 | Aoki | B60N 2/5657 62/3.3 |
| 2009/0000310 | A1 * | 1/2009 | Bell | B60H 1/00885 62/3.7 |
| 2012/0174607 | A1 * | 7/2012 | Cur | F25D 17/02 62/186 |
| 2016/0257181 | A1 * | 9/2016 | Zhou | B60H 1/32014 |

FOREIGN PATENT DOCUMENTS

| | | |
|---|---|---|
| JP | 4-332557 A | 11/1992 |
| JP | 5-17470 U | 3/1993 |
| JP | 7-101138 B2 | 11/1995 |
| JP | 2000-270837 A | 10/2000 |
| JP | 2002-282136 A | 10/2002 |
| JP | 2008-534905 A | 8/2008 |
| JP | 2009-223838 A | 10/2009 |

OTHER PUBLICATIONS

Japanese-language Written Opinion (PCT/ISA/237) issued in PCT Application No. PCT/JP2016/069116 dated Sep. 13, 2016 (eight (8) pages).

* cited by examiner

REFRIGERATING/HEATING DEVICE, AND ANALYSIS DEVICE

TECHNICAL FIELD

The present invention relates to a refrigerating/heating device and an analysis device using the same, and particularly to a refrigerating/heating device technology capable of reducing costs with a simple structure.

BACKGROUND ART

Components used for cooling and heating of the refrigerating/heating device are generally a heat pump, a heater, Peltier, a compressor and the like. In addition, in a case where there are a cooling chamber, a heating chamber, and the like in a device and the cooling chamber and the heating chamber are simultaneously cooled and heated, respectively, it is necessary to use two of the above components. That is, there is no device that cools and heats two regions respectively with only one component.

As a device that simultaneously performs cooling and heating, PTL 1 discloses a cooling and heating device using a cooling heat pump, a heating heat pump, and a sheath heater. In PTL 1, there is provided a configuration in which a condenser of the cooling heat pump, a compressor of the cooling heat pump, and an evaporator of the heating heat pump are disposed from an upstream side in this order, along an air flow direction, accordingly, air heated by exhaust heat of the condenser of the cooling heat pump comes into contact with the compressor of the cooling heat pump and is further heated, and the heated air is introduced into the evaporator of the heating heat pump so as to further raise an evaporation temperature in the evaporator, accordingly, it is possible to improve a thermal efficiency of the heating heat pump.

In addition, PTL 2 discloses an incubator using a Peltier cooler and a Peltier heater. A first Peltier element for heating a heating block, a second Peltier element for cooling the cooling block by a heat absorbing surface, and a thermal conductive connecting member that connects the heat absorbing surface of the first Peltier element with a heat radiating surface of the second Peltier element are provided and heat energy generated from the heat radiating surface of the second Peltier element is recovered by the heat absorbing surface of the first Peltier element and is utilized for heating the heating block for achieving the efficiency improvement and durability improvement.

CITATION LIST

Patent Literature

PTL 1: JP-A-2009-223838
PTL 2: JP-A-2000-270837

SUMMARY OF INVENTION

Technical Problem

In the PTL 1 described above, two independent temperature adjusting components respectively for cooling and heating are arranged, and heat generation of the cooling heat pump is diverted to the thermal efficiency improvement of the heating heat pump. In a case where two areas with different temperature settings are provided and cooling and heating are simultaneously performed on the areas, such a system is generally used. However, since a plurality of components for temperature control are required, the costs increase, and a size of a device also increases.

In PTL 2, one device has regions with different temperature settings of a cooling part and a heating part (the cooling block and the heating block) therein. The temperature adjustment component is a Peltier element, and the heat absorbing surface of a heating Peltier element and the heat radiating surface of a cooling Peltier element are connected by the thermal conductive connecting member for achieving overall efficiency improvement. However, since two Peltier elements are used and the temperature control for cooling or heating is required for each Peltier element, as in PTL 1, a plurality of mechanical elements for temperature control are required, the costs increase and a size of a device also increases.

In order to solve the above problems, an object of the present invention is to provide a refrigerating/heating device which is capable of performing refrigerating and heating with one Peltier element for a device having a refrigeration part and a heating part of temperature setting and is low in costs, and is to provide an analysis device using the same.

Solution to Problem

In order to achieve the above object, in the present invention, there is provided a refrigerating/heating device having a configuration including: a refrigeration chamber; a Peltier-type cooler that supplies cold air to an inside of the refrigeration chamber; a heat radiation member for radiating Peltier heat; a fan for air-cooling the heat radiation member; and an installation part which is provided in a flow path through which waste heat from the fan and the heat radiation member passes, and to which a subject to be heated can be installed, wherein the subject to be heated is installed to the installation part and heated.

In addition, in order to achieve the above object, there is provided a refrigerating/heating device having a configuration including: a refrigeration chamber; a Peltier-type cooler that supplies cold air to an inside of the refrigeration chamber; a heat radiation member for radiating Peltier heat; a fan for air-cooling the heat radiation member; a temperature measurement unit that measures a temperature of waste heat from the fan and the heat radiation member; an installation part to which a subject to be heated can be installed; and a flow path switching part that switches an exhaust route capable of heat exchange between the subject to be heated installed to the installation part and the waste heat and an exhaust route not performing heat exchange between the waste heat and the subject to be heated, wherein the flow path switching part switches the two exhaust routes based on a measurement result of the temperature measurement unit.

In addition, in order to achieve the above object, there is provided a refrigerating/heating device in which substantially single Peltier element is used as a heat source, a heat absorbing part of a Peltier element and a refrigeration part are directly or indirectly joined, and a heat generating part of the Peltier element and an installation part of a subject to be heated are directly or indirectly joined. In addition, the refrigerating/heating device may control the Peltier element such that a temperature of the refrigeration part becomes a desired temperature, a heat radiation member such as fins may be provided to the heat generating part of the Peltier element, and waste heat may be conveyed to the installation part of a subject to be heated via an exhaust duct by fan for air-cooling. Further, the refrigerating/heating device may be provided with a temperature sensor in the exhaust duct, a flow rate adjusting mechanism that adjusts a flow rate conveyed to the installation part of a subject to be kept warm through the exhaust duct, within 0% to 100%, and a plurality of installation parts of subjects to be kept warm.

Further, in order to achieve the above object, there is provided an analysis device having a configuration including: the refrigerating/heating device mounted thereon, in which a reagent to be refrigerated is refrigerated in a refrigeration chamber, and a reagent to be kept warm is installed to the installation part.

Advantageous Effects of Invention

According to the present invention, it is possible to provide a refrigerating/heating device which is capable of performing refrigerating and heating with one Peltier and is low in costs.

BRIEF DESCRIPTION OF DRAWINGS

FIG. 4 is a diagram illustrating a relationship between a room temperature and waste heat-room temperature of the refrigerating/heating device according to Example 1.

DESCRIPTION OF EMBODIMENTS

Hereinafter, various examples of the present invention will be described in detail with reference to the drawings.

Example 1

Example 1 is an example of a refrigerating/heating device including a refrigeration chamber, a Peltier-type cooler that supplies cold air to an inside of the refrigeration chamber, a heat radiation member for radiating Peltier heat, a fan for air-cooling the heat radiation member, and an installation part which is installed to a flow path through which waste heat from the fan and the heat radiation member passes, and to which a subject to be heated can be installed, wherein the subject to be heated is installed to the installation part and heated.

Figure 1A:
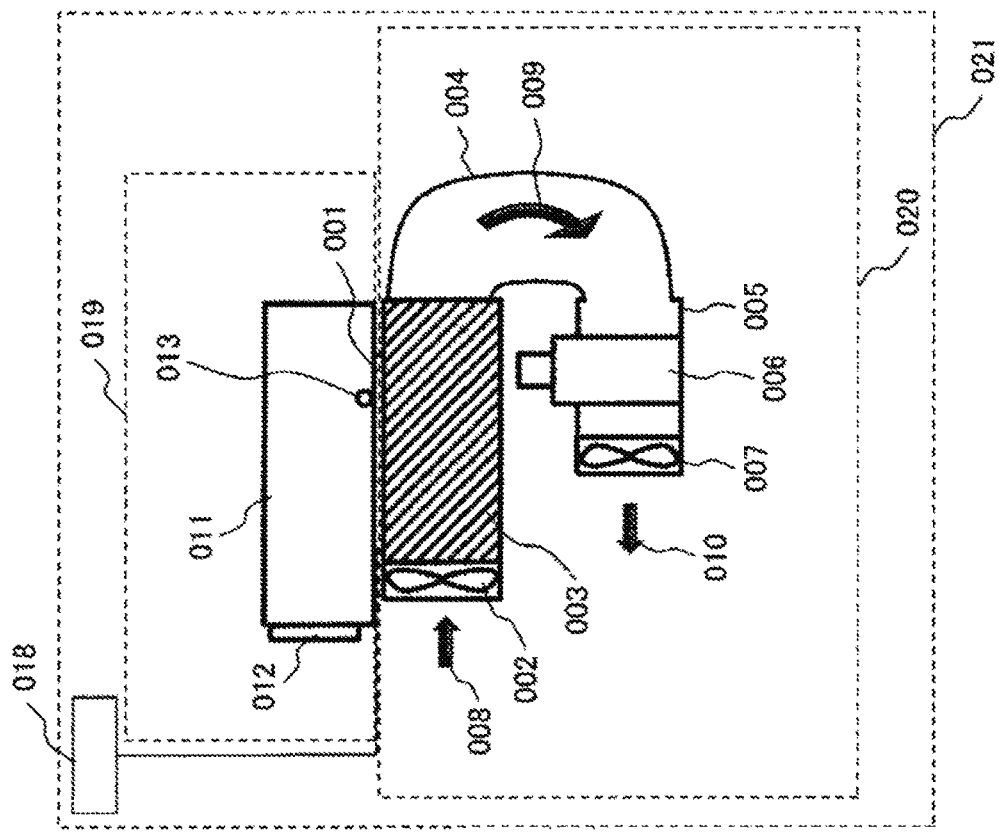
FIGS. 1A and 1B are diagrams illustrating a configuration example of a refrigerating/heating device according to Example 1.
Figure 1B:
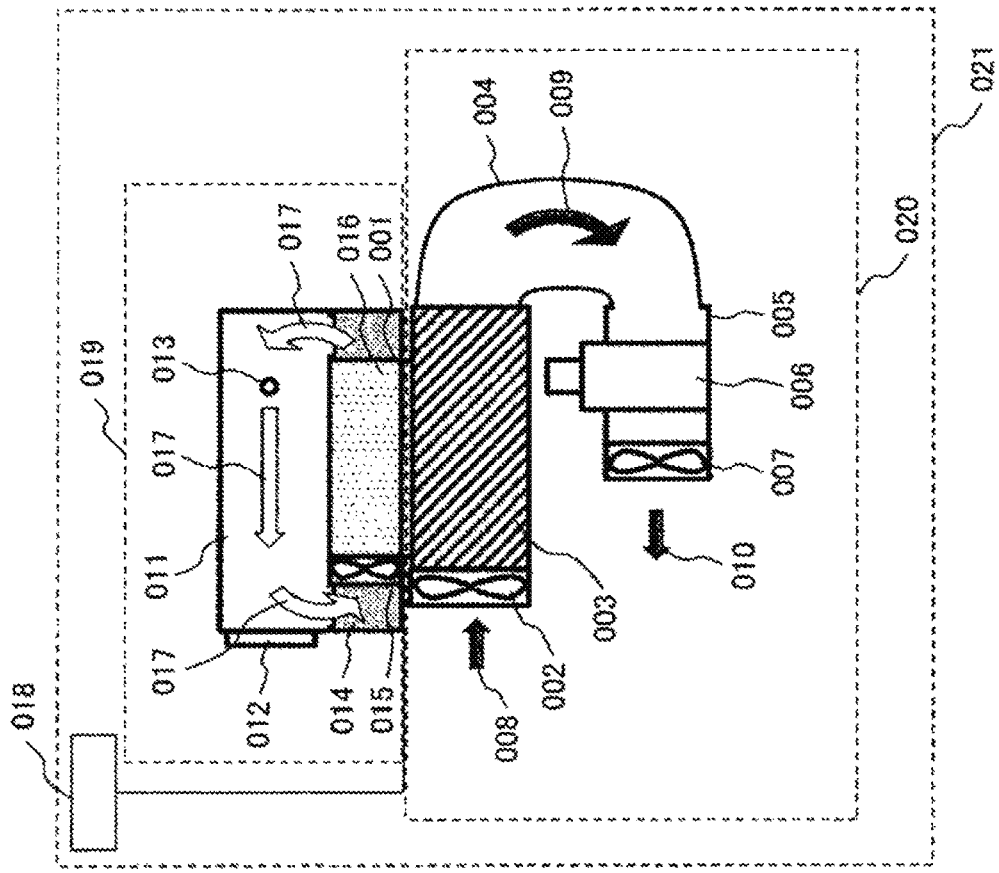

FIG. 1 is a diagram illustrating a configuration example of a refrigerating/heating device according to Example 1. As illustrated in FIG. 1, a refrigerating/heating device 21 according to the present example is configured to include a control unit 18, a refrigeration part 19, and a heating part 20. (a) of FIG. 1 shows a refrigerating/heating device using heat transfer and heat conduction, (b) of FIG. 1 shows a refrigerating/heating device using heat conduction.

In (a) of FIG. 1, the refrigeration part 19 is configured of a Peltier 1 configuring a Peltier-type cooler, a refrigeration chamber 11, a refrigeration chamber door 12, a temperature measurement unit 13, a cover 14, a fan 15, and a cooling member 16, and the heating part 20 is configured of a fan 2, a heat radiation member for radiating Peltier heat, an exhaust duct 4, an installation part of a subject to be heated, and a fan 7. Here, as the temperature measurement unit 13, a thermocouple, a thermistor, a resistance temperature detector, an integrated circuit (IC) temperature sensor, or the like is used.

Cooling in the refrigerating/heating device 21 according to the present example is performed by controlling a current or a voltage flowing from the control unit 18 to the Peltier 1 such that a temperature of the temperature measurement unit 13 in the refrigeration chamber 11 becomes within 5° C.±2° C. When the Peltier 1 starts cooling control, a temperature of the cooling member 16 decreases and a temperature of the heat radiation member 3 increases. The cooling part 19 causes air 17 in the refrigeration chamber 11 to be circulated by the fan 15, and the temperature in the refrigeration chamber 11 to be cooled and refrigerated. Access to the inside of the refrigeration chamber 11 is performed by the refrigeration chamber door 12.

In addition, since cooling efficiency of the Peltier 1 is better as a temperature difference (Δt) between a heat absorbing surface and a heat radiating surface is smaller, the heat radiation member 3 is air-cooled by the fan 2. The air 8 which is sucked by fan 2 absorbs the heat of the heat radiation member and becomes waste heat 9, and is supplied through the exhaust duct 4 which constitutes a flow path thereof to the installation part 5 of a subject to be heated, which is installed on the flow path, via the exhaust duct 4 serving as the flow path thereof, and heats the subject 6 to be heated. The waste heat 9 which has lost energy by the subject 6 to be heated becomes waste heat 10 and is discharged to an outside of the refrigerating/heating device. In the configuration illustrated in FIG. 1, two fans 2 and 7 are shown; however, only one of them may be installed.

In the configuration of the refrigerating/heating device using heat conduction, illustrated in (b) of FIG. 1, the Peltier 1 and the refrigeration chamber 11 are brought into contact with each other to cool and refrigerate the inside of the refrigeration chamber through the heat conduction. Other configurations are the same as the configuration of (a) of FIG. 1, and a current or a voltage flowing from the control unit 18 to the Peltier 1 is controlled such that the temperature of the temperature measurement unit 13 in the refrigeration chamber 11 becomes within 5° C.±2° C.

Figure 2A:
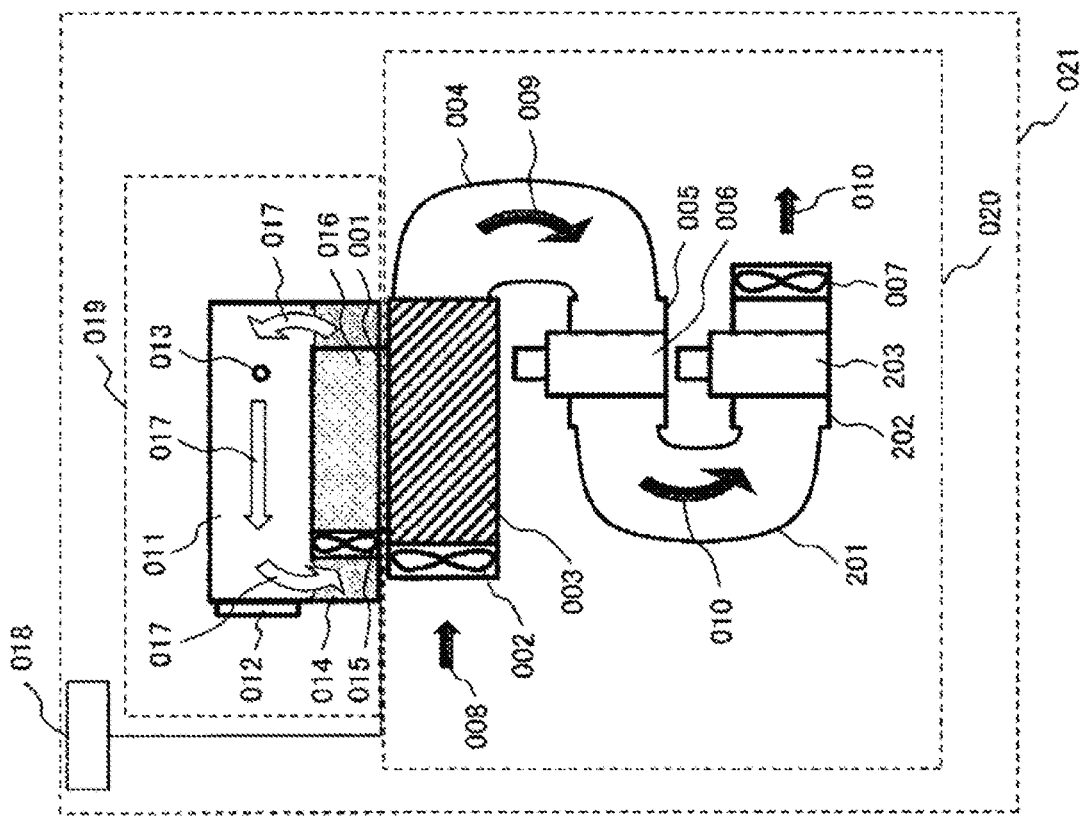
FIGS. 2A and 2B are diagrams illustrating a modification example of the refrigerating/heating device according to Example 1.
Figure 2B:
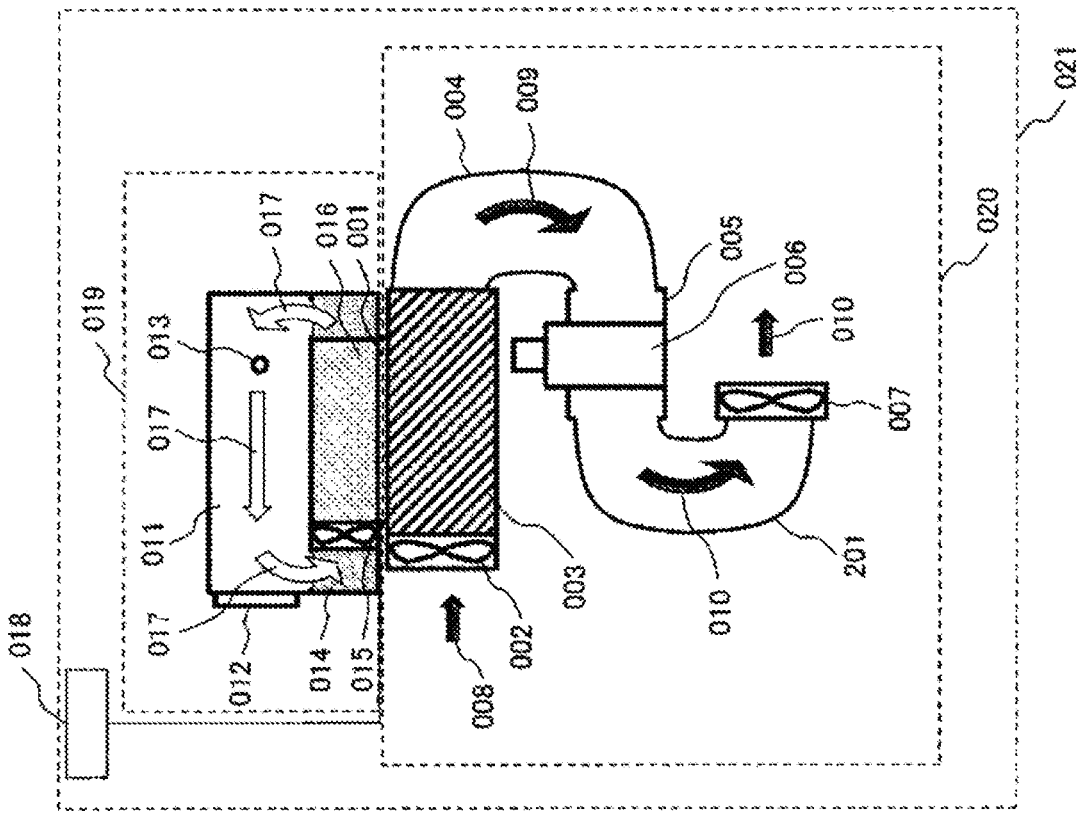
Figure 3A:
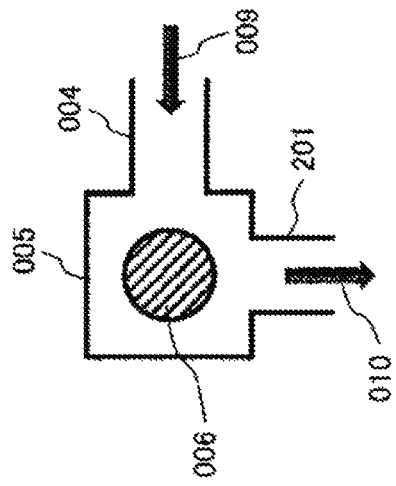
FIGS. 3A through 3E are diagrams illustrating a flow path example of waste heat of the refrigerating/heating device according to Example 1.
Figure 3B:
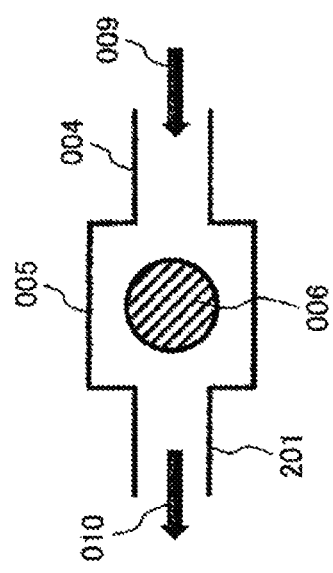
Figure 3C:
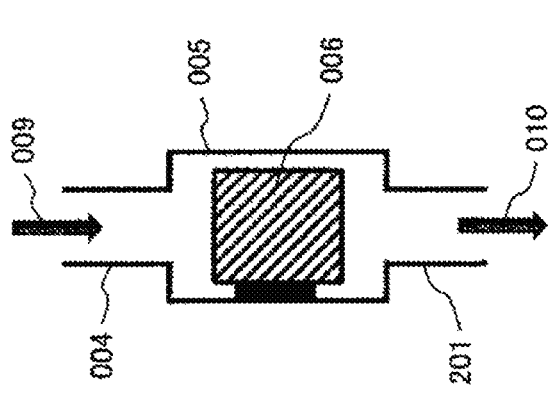
Figure 3D:
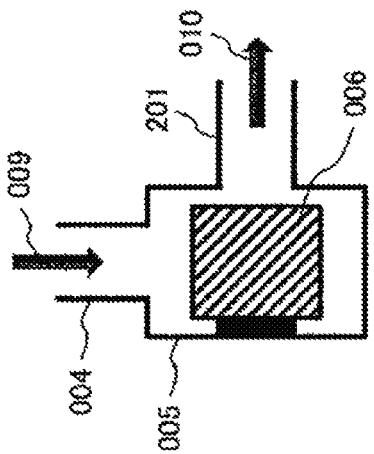
Figure 3E:
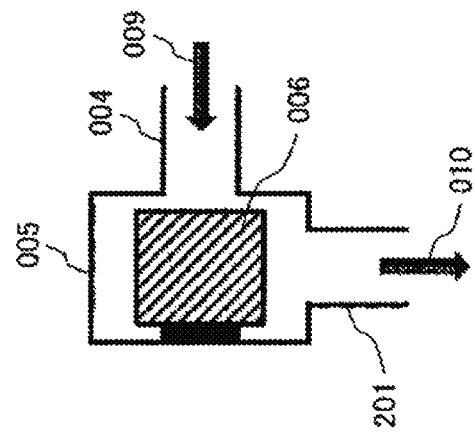

FIG. 2 illustrates a configuration of a modification example of the refrigerating/heating device according to Example 1. In (a) of FIG. 2, in order for the waste heat 10 to be discharged from a specific outlet, an exhaust duct 201 serving as a flow path is further included on a downstream of the installation part 5 of a subject to be heated. In (b) of FIG. 2, an installation site 202 of a subject to be heated and a subject 203 to be heated, which are added to the exhaust duct 201 on the downstream of the installation site 5 of a subject to be heated, are further included.

As the configuration of the modification example illustrated in (a) and (b) of FIG. 2, in the configuration of the refrigerating/heating device of FIG. 1, there may be more than one exhaust ducts, installation sites of a subject to be heated, and the subjects to be heated may be 2 or more.

FIG. 3 is a diagram illustrating a configuration example of the flow path of waste heat of the refrigerating/heating device according to the present example. (a) and (b) of FIG. 3 show plan views of the exhaust duct 4, the installation part 5 of a subject to be heated, the subject 6 to be heated, and the exhaust duct 201. (c), (d), and (e) of FIG. 3 show vertical sectional views of the exhaust duct 4, the installation part 5 of a subject to be heated, the subject 6 to be heated, and the exhaust duct 201.

In (a) of FIG. 3, a positional relationship of the exhaust duct 4 and the exhaust duct 201 which are the flow paths is on a straight line, that is, 0° and the waste heat 9 is positively brought into contact with the subject 6 to be heated to perform heat exchange. In (b) of FIG. 3, the exhaust duct 4 and the exhaust duct 201 which are the flow paths are disposed in a position of a right angle, that is, 90°. In the above configuration examples, positions of 0° and 90° were shown, but the connection may be made in a preferable position between 0° and 180°.

In (c) of FIG. 3, the exhaust duct 4 and the exhaust duct 201 which are the flow paths are disposed linearly in a gravity direction. The subject 6 to be heated is installed from aside face of the installation part 5 of a subject to be heated and becomes in a state of floating in the air. However, the subject 6 to be heated may be installed on a bottom face of the installation part 5 of a subject to be heated, as long as the subject 6 to be heated does not block a vent hole of the exhaust duct 201. In (d) of FIG. 3, the exhaust duct 4 is connected to a top face of the installation part 5 of a subject to be heated and the exhaust duct 201 is connected to a side face of the installation part 5 of a subject to be heated. The subject 6 to be heated is installed from the side face of the installation part 5 of a subject to be heated, and becomes a state of floating in the air or of being in contact with the bottom face of the installation part 5 of a subject to be heated. A hole may be drilled in the bottom face of the installation part 5 of a subject to be heated, and the subject 6 to be heated may be installed from the bottom face of the installation part 5 of a subject to be heated.

In (e) of FIG. 3, the exhaust duct 4 is connected to a side face of the installation part 5 of a subject to be heated and the exhaust duct 201 is connected to the bottom face of the installation part 5 of a subject to be heated. The subject 6 to be heated is installed from a side face of the installation part 5 of a subject to be heated and becomes in a state of floating in the air. However, the subject 6 to be heated may be installed on a bottom face of the installation part 5 of a subject to be heated, as long as the subject 6 to be heated does not block a vent hole of the exhaust duct 201. In (e) of FIG. 3, the subject 6 to be heated is installed in the installation part 5 of a subject to be heated. However, a hole may be drilled in the top face of the installation part 5 of a subject to be heated and the subject 6 to be heated may be in a state of protruding from the hole of the top face of the installation part 5 of a subject to be heated. In this case, for installing the subject 6 to be heated, it is possible to access from the hole of the top face of the installation part 5 of a subject to be heated.

FIG. 4 is a graph illustrating an example of a relationship between a room temperature and waste heat-room temperature, in the refrigerating/heating device according to the present example. The temperature of the waste heat is a temperature obtained by measuring a temperature of the waste heat 9 on a downstream of the heat radiation member 3. A horizontal axis of the same figure shows a room temperature (° C.) and a vertical axis shows the relation of waste heat-room temperature (° C.). The data of FIG. 4 is data during a steady state of the cooling control of the refrigeration chamber. It is possible to supply waste heat of room temperature+approximately 2.6° C. under an environment of room temperature of 18° C. to 25° C.

In the data shown in FIG. 4, waste heat has a temperature of room temperature+approximately 2.6° C. However, depending on a shape and a material of the heat radiation member and selection of Peltier 1, it is possible to further increase the temperature of waste heat to be supplied. As the materials of the cooling member 16 and the heat radiation member 3, aluminum, copper, gold, silver, other synthetic metals, heat conduction resin, and the like can be used. As the shape thereof, a pinholder shaped object, an object with many fins, an object with pillars side by side, and the like can be used.

According to the present example, it is possible to provide a refrigerating/heating device which is capable of performing refrigerating and heating with a simple configuration of one Peltier and is low in costs.

According to the present example, an operation of the Peltier element is controlled based on the temperature of the refrigeration chamber, and only by the control, it is possible to heat a subject to be kept warm approximately from 21° C. to 28° C. (room temperature (18° C. to 26° C.)). It is possible to configure the refrigerating/heating device with one Peltier element and one control device, and it is possible to reduce the size and costs. In addition, it was confirmed that the temperature of the heat generating part of the Peltier element was higher than the temperature of the heating part and by using this heat as it is for the heating part, it is possible to secure the sufficient heating performance. By using the heat of the heat generating part for the heating part, it is possible to construct a heating part which is simple and low in costs.

Example 2

Figure 5A:
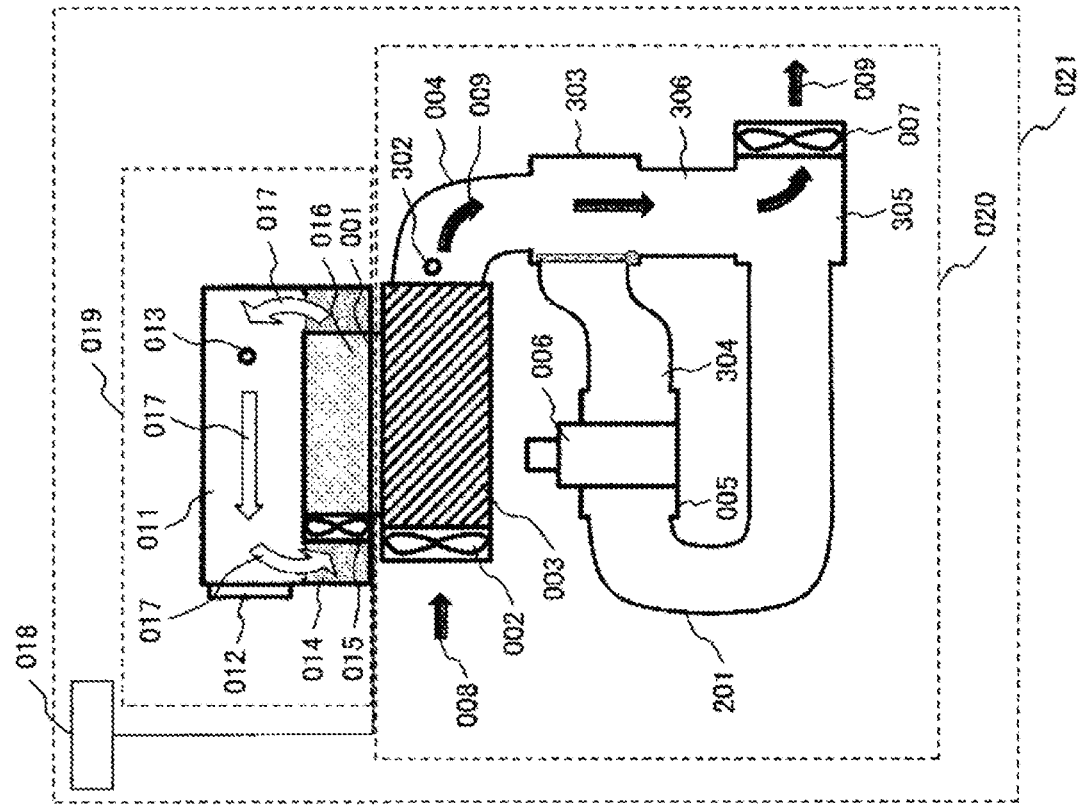
FIGS. 5A and 5B are diagrams illustrating a configuration example of a refrigerating/heating device according to Example 2.
Figure 5B:
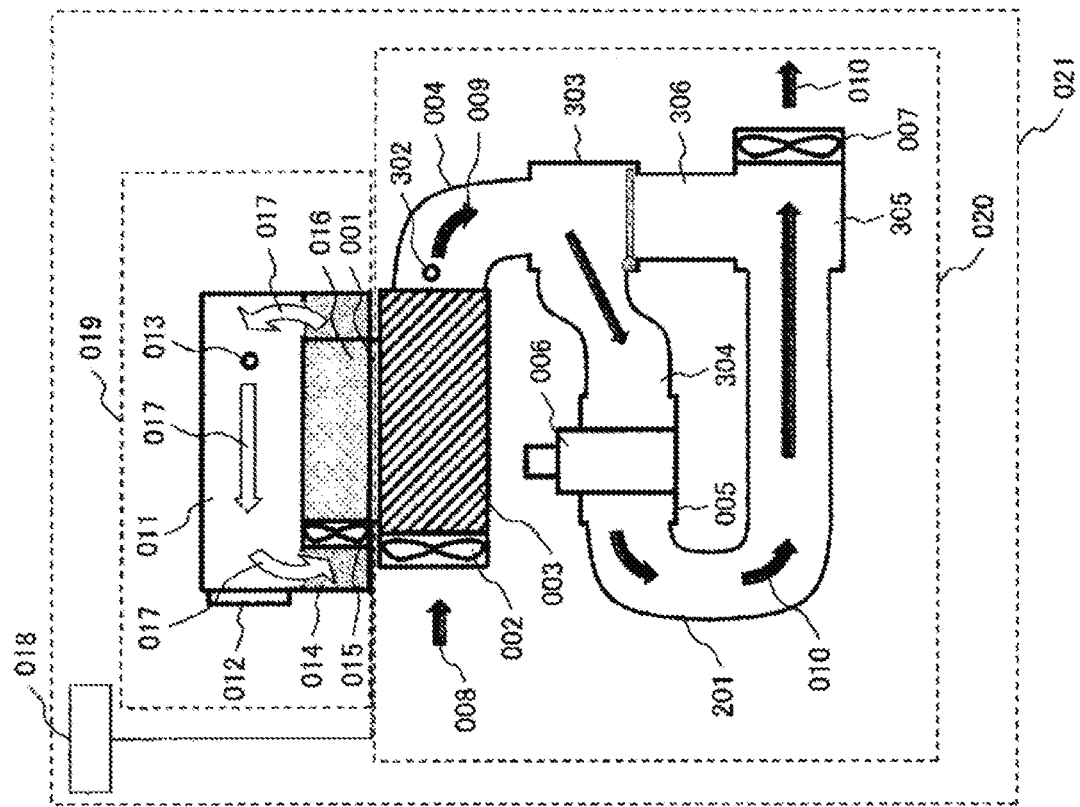

Example 2 is an example of a refrigerating/heating device having a configuration further including a flow path switching part capable of switching exhaust routes based on the measured temperature of the temperature measurement unit provided in the exhaust duct, in addition to the configuration of Example 1, in which it is possible to switch an exhaust route capable of heat exchange between the waste heat and the subject to be heated and an exhaust route not performing heat exchange between the waste heat and the subject to be heated. In FIG. 5, a configuration of the refrigerating/heating device related to the present example is shown.

In FIG. 5, a refrigeration part 19 is configured of a Peltier 1, a refrigeration chamber 11, a refrigeration chamber door 12, a temperature measurement unit 13, a cover 14, a fan 15, and a cooling member 16, and a heating part 20 is configured of a fan 2, a heat radiation member 3, an exhaust duct 4, an installation site 5 of a subject to be heated, a fan 7, a temperature measurement unit 302 that measures the temperature of waste heat, a flow path switching part 303, an exhaust duct 201, an exhaust duct 304, an exhaust duct 306, and waste heat dissipating unit 305. As in the temperature measurement unit 13, a thermocouple, a thermistor, a resistance temperature detector, an IC temperature sensor, or the like is used as the temperature measurement unit 302.

Cooling and refrigerating are the same as in Example 1, and a current or a voltage flowing from the control unit 18 to the Peltier 1 is controlled such that the temperature of the temperature measurement unit 13 in the refrigeration chamber 11 becomes within 5° C.±2° C. When the Peltier 1 starts cooling control, a temperature of the cooling member 16 decreases and a temperature of the heat radiation member 3 increases. The refrigeration part 19 causes air 17 in the refrigeration chamber 11 to be circulated by the fan 15, and the temperature in the refrigeration chamber 11 to be cooled and refrigerated. Access to the inside of the refrigeration chamber 11 is performed by the refrigeration chamber door 12.

The heat radiation member 3 is air-cooled using the fan 2. The air 8 which is sucked by fan 2 absorbs the heat of the heat radiation member and becomes waste heat 9, and is supplied to the flow path switching part 303, via the exhaust duct 4. In addition, the temperature of the waste heat 9 is measured with the temperature measurement unit 302 in the exhaust duct 4. Based on the measured temperature, the flow path switching part 303 is controlled to switch flow paths, that is, between an exhaust route capable of heat exchange between the waste heat and the subject to be heated and an exhaust route not performing heat exchange between the waste heat and the subject to be heated.

(a) of FIG. 5 shows a diagram illustrating a flow path that supplies waste heat 9 to the installation part 5 of a subject to be heated, in the configuration of the present example. In a case where the measured temperature of the waste heat 9 by the temperature measurement unit 302 is 30° C. or lower, the flow path switching part 303 connects the flow path to an exhaust duct 304 side, supplies the waste heat 9 to the installation site 5 of a subject to be heated, and heats the subject 6 to be heated. The waste heat 9 which has lost energy by the subject 6 to be heated becomes the waste heat 10 and is discharged to an outside of the waste heat dissipating unit 305. In FIG. 5, two fans 2 and 7 are shown; however, only one of them may be installed.

(b) of FIG. 5 shows a diagram illustrating a flow path not supplying the waste heat 9 to the installation part 5 of a subject to be heated. In a case where the temperature of the temperature measurement unit 302 exceeds 30° C., the flow path switching part 303 is connected to the exhaust duct 306 and discharges the waste heat 9 from the waste heat dissipating unit 305 directly to the outside of the device.

Figure 6A:
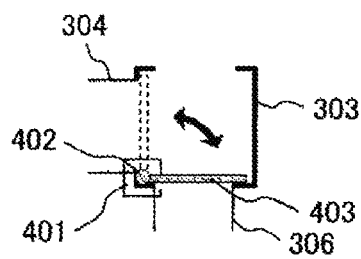
FIGS. 6A through 6C are diagrams illustrating a configuration example of a flow path switching part of the refrigerating/heating device according to Example 2.
Figure 6B:
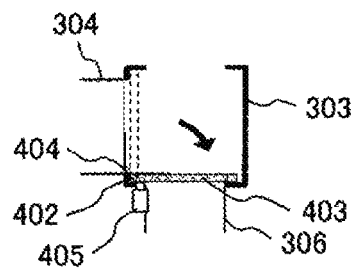
Figure 6C:
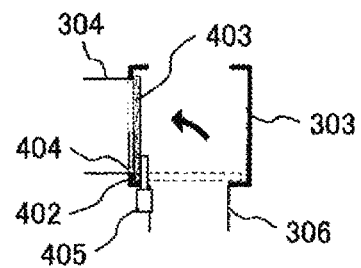

FIG. 6 is a diagram illustrating a specific configuration example of the flow path switching part of the refrigerating/heating device according to the present example. (a) of FIG. 6 shows a configuration in which a stepping motor 401 causes a flow path switching shaft 402 and a flow path switching plate 403 to pivot so as to switch the flow paths. (b) and (c) of FIG. 6 show a configuration for switching the flow paths by using a spring 404 and a solenoid 405. When supplying a power to the solenoid 405, the flow path switching plate 403 is pushed to an exhaust duct 304 side by force of the solenoid 405, and the flow path becomes a flow path of the exhaust duct 306. During non-supply, the flow path switching plate 403 is pushed to an exhaust duct 306 side by force of the spring 404, and the flow path becomes a flow path of exhaust duct 304. The mechanical elements may be reversely used and the connection destination may be reversed. In addition, thermoelement and the like may be used instead of the solenoid 405.

FIG. 6 shows an example of a case of 0% and 100% switching to a subject to be heated, but by setting the flow path switching plate to an intermediate position, it is possible to be set to a certain position within 0% to 100%.

According to the refrigerating/heating device of the present example, by measuring the temperature of the waste heat in the exhaust duct, it is possible to prevent a subject to be heated from unnecessarily being heated.

In this example, as in Example 1, there is one Peltier element, and control thereof is performed based on the temperature of the refrigeration chamber. In addition, the control of the flow path switching part is possible to perform an operation with a simple structure and low electric power. Accordingly, it is possible to reduce the size and costs.

Example 3

Example 3 is an example of an analysis device in which the refrigerating/heating device of Example 1 or 2 is mounted and used. That is, the configuration and function of the refrigerating/heating device described above are installed in the analysis device, refrigerating of a reagent to be refrigerated is performed in the refrigeration chamber 11 which is the refrigeration part, and heating is performed by installing a reagent to be kept warm to the installation part 5 of the heating part. As the reagent to be kept warm in the analysis device, reagents and the like which need to be prevented from crystallizing are targeted.

According to the present invention described above, it is possible to provide a refrigerating/heating device and an analysis device, which are capable of performing refrigerating and heating with a simple configuration of one Peltier and are low in costs and small in size. Further, it is possible to prevent the subject to be heated from unnecessarily being heated.

The present invention is not limited to the above examples, and includes various modification examples. For example, the above examples have been described in detail in order to explain the present invention in an easy-to-understand manner, and are not necessarily limited to those having all the described configurations. In addition, it is possible to replace apart of the configuration of a certain example with the configuration of other examples, and it is also possible to add the configuration of other examples to the configuration of a certain example. In addition, it is also possible to add other configurations, delete, or replace with respect to a part of the configuration of each Example.

REFERENCE SIGNS LIST

1: Peltier
2, 15: Fan
3: Heat radiation member
4, 201, 304, 306: Exhaust duct
5, 202: Installation part
6, 203: Subject to be heated
7: Fan
8, 17: Air
9: Waste heat
10: Waste heat
11: Refrigeration chamber
12: Refrigeration chamber door
13, 302: Temperature measurement unit
14: Cover
16: Cooling member
18: Control unit
19: Cooling part
20: Heating part
21: Cooling and heating device
303: Flow path switching part
305: Waste heat dissipating unit
401: Stepping motor
402: Flow path switching shaft
403: Flow path switching plate
404: Spring
405: Solenoid

The invention claimed is:

1. A refrigerating/heating device comprising:
a refrigeration chamber;
a Peltier-type cooler that supplies cold air to an inside of the refrigeration chamber;
a heat radiation member for radiating Peltier heat;
a fan for air-cooling the heat radiation member;
a temperature measurement unit that measures a temperature of waste heat from the fan and the heat radiation member;

an exhaust duct to which a subject to be heated is installed; and a flow path switching part that switches between a first exhaust route capable of heat exchange between the subject to be heated installed to the exhaust duct and the waste heat and a second exhaust route not performing heat exchange between the waste heat and the subject to be heated, wherein the flow path switching part switches between the first and second exhaust routes based on a measurement result of the temperature measurement unit, the first and second exhaust routes respectively include a first and second exhaust duct, and the flow path switching part includes a flow path switching plate that switches the flow path to any of the first and second exhaust ducts.

2. The refrigerating/heating device according to claim 1, wherein the fan, the heat radiation member, the temperature measurement unit, and the flow path switching part are disposed in this order, from an upstream side along an air flow direction.

3. The refrigerating/heating device according to claim 1, wherein the flow path switching part includes a stepping motor that causes the flow path switching plate to pivot on a flow path switching shaft.

4. The refrigerating/heating device according to claim 1, wherein the flow path switching part includes a spring and a solenoid or a thermoelement that causes the flow path switching plate to pivot on the flow path switching shaft.

5. An analysis device comprising:
the refrigerating/heating device according to claim 1 mounted on the analysis device,
wherein a reagent to be refrigerated is refrigerated in the refrigeration chamber, and
a reagent to be kept warm is installed to the exhaust duct.

6. A refrigerating/heating device including a refrigeration part and a heating part that heats a subject to be heated, the device comprising:
a single Peltier element;
wherein a heat absorbing part of the single Peltier element and the refrigeration part are joined together,
a heat generating part of the single Peltier element and the heating part are joined together,
a Peltier element control unit that controls the single Peltier element only based on temperature information of the refrigeration part; and
the heat generating part of the single Peltier element being provided with a heat radiation member and a fan for air-cooling and is connected to an exhaust duct of the subject to be heated via the exhaust duct,
a temperature sensor for measuring a temperature inside the exhaust duct and a flow path switching part that changes a flow path inside the exhaust duct to the exhaust duct of the subject to be heated are included between the single Peltier element and the exhaust duct of the subject to be heated,
the flow path switching part being configured to divide waste heat from the heat generating part of the single Peltier element and to supply a part of the waste heat to the exhaust duct of the subject to be heated.

7. The refrigerating/heating device according to claim 6, wherein the flow path switching part turns ON/OFF supply of the waste heat from the heat generating part of the single Peltier element to the exhaust duct of the subject to be heated.

8. An analysis device comprising:
the refrigerating/heating device according to claim 6 mounted on the analysis device,
wherein a reagent to be refrigerated is refrigerated in the refrigeration part, and
a reagent to be kept warm is installed to the heating part.

* * * * *